United States Patent
Ishikawa et al.

(10) Patent No.: US 9,592,219 B2
(45) Date of Patent: Mar. 14, 2017

(54) SELF-MAGNETIC METAL-SALEN COMPLEX COMPOUND

(75) Inventors: Yoshihiro Ishikawa, Tokyo (JP); Haruki Eguchi, Tokyo (JP)

(73) Assignees: IHI Corporation, Tokyo (JP); Yoshihiro Ishikawa, Tokyo (JP)

( * ) Notice: Subject to any disclaimer, the term of this patent is extended or adjusted under 35 U.S.C. 154(b) by 365 days.

(21) Appl. No.: 14/234,801

(22) PCT Filed: May 14, 2012

(86) PCT No.: PCT/JP2012/062301
§ 371 (c)(1),
(2), (4) Date: Jul. 14, 2014

(87) PCT Pub. No.: WO2013/014997
PCT Pub. Date: Jan. 31, 2013

(65) Prior Publication Data
US 2014/0323566 A1    Oct. 30, 2014

(30) Foreign Application Priority Data

Jul. 26, 2011 (JP) .................. 2011-163621

(51) Int. Cl.

| | |
|---|---|
| A61K 31/555 | (2006.01) |
| A61K 31/295 | (2006.01) |
| C07C 251/08 | (2006.01) |
| C07C 251/12 | (2006.01) |
| C07C 251/24 | (2006.01) |
| A61K 41/00 | (2006.01) |
| A61K 47/48 | (2006.01) |
| A61K 49/10 | (2006.01) |
| C07F 15/02 | (2006.01) |

(52) U.S. Cl.
CPC ............ *A61K 31/295* (2013.01); *A61K 41/00* (2013.01); *A61K 47/4893* (2013.01); *A61K 49/103* (2013.01); *C07C 251/08* (2013.01); *C07C 251/12* (2013.01); *C07C 251/24* (2013.01); *C07F 15/025* (2013.01)

(58) Field of Classification Search
USPC ........................................................ 514/185
See application file for complete search history.

(56) References Cited

U.S. PATENT DOCUMENTS

| | | | |
|---|---|---|---|
| 5,403,834 | A | 4/1995 | Malfroy-Camine et al. |
| 5,549,915 | A | 8/1996 | Volkonsky et al. |
| 6,344,516 | B1 | 2/2002 | Ikeda et al. |
| 2009/0169484 | A1 | 7/2009 | Eguchi et al. |
| 2009/0311163 | A1 | 12/2009 | Eguchi et al. |
| 2012/0029167 | A1 | 2/2012 | Ishikawa |
| 2012/0259155 | A1 | 10/2012 | Ishikawa |
| 2013/0090539 | A1 | 4/2013 | Ishikawa et al. |
| 2013/0131367 | A1 | 5/2013 | Ishikawa et al. |
| 2014/0011032 | A1 | 1/2014 | Ishikawa |
| 2014/0046021 | A1 | 2/2014 | Ishikawa |
| 2014/0235883 | A1 | 8/2014 | Eguchi |
| 2014/0302604 | A1 | 10/2014 | Ishikawa |

FOREIGN PATENT DOCUMENTS

| | | |
|---|---|---|
| CN | 101967112 A | 2/2011 |
| EP | 0726077 A2 | 8/1996 |
| EP | 2357166 A1 | 8/2011 |
| EP | 2517752 A1 | 10/2012 |
| EP | 2657223 A1 | 10/2013 |
| EP | 2682384 A1 | 1/2014 |
| EP | 2733713 A1 | 5/2014 |
| EP | 2772522 A1 | 9/2014 |
| JP | 5-9470 A | 1/1993 |
| JP | 05-009470 A | 1/1993 |
| JP | 8-504211 A | 5/1996 |
| JP | 08-504211 A | 5/1996 |
| JP | 2001-010978 A | 1/2001 |
| JP | 2008115129 A | 9/2008 |
| JP | 2009-173631 A | 8/2009 |
| JP | 2009196913 A | 9/2009 |
| JP | 2009196914 A | 9/2009 |
| JP | 2011-153239 A | 8/2011 |
| WO | 9413300 A1 | 6/1994 |
| WO | 9618402 A1 | 6/1996 |
| WO | 01/00702 A1 | 1/2001 |

(Continued)

OTHER PUBLICATIONS

International Search Report dated Aug. 5, 2015.
International Search Report from corresponding International Application No. PCT/JP2012/062301 mailed Jul. 31, 2012.
Belanzoni, P. et al, A theoretical approach to a chemical system convertible into a storage cell: carbon-carbon bonds functioning as electron donor and electron acceptor units, Journal of Molecular Catalysis A: Chemical, 2003, vol. 204-205, pp. 787-792.
Howells, P.N. et al., Reactions of (4, 9-dimethyl-5, 8-diazadodeca-4, 8-diene-2, 11-dione)copper (II), (Cu(baen)) with isocyanates, Inorganic Chemistry, 1976, vol. 15, No. 1, p. 124.
Evreev, V.N. et al, Cobalt (II) complexes with N, N'-diethanolethylenediamine, Koordinatsionnaya Khimiya, 1978, vol. 4, No. 2, p. 254-9.

(Continued)

*Primary Examiner* — Charanjit Aulakh
(74) *Attorney, Agent, or Firm* — Brundidge & Stanger, P.C.

(57) ABSTRACT

A new self-magnetic metal-salen complex compound and its derivatives are provided. The present invention is a metal-salen complex compound including any one of the following compounds.

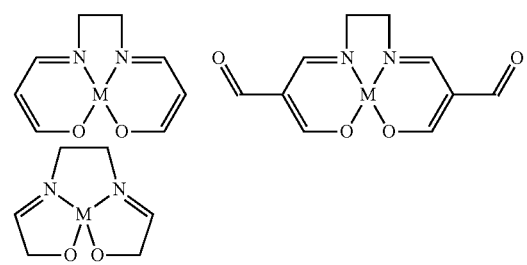

20 Claims, 6 Drawing Sheets

(56) References Cited

FOREIGN PATENT DOCUMENTS

| WO | 2008/001851 A1 | 1/2008 |
| WO | 2008/090081 A1 | 7/2008 |
| WO | 2010058280 A1 | 5/2010 |
| WO | 2011077750 A1 | 6/2011 |
| WO | 2011/135784 A1 | 11/2011 |
| WO | 2011/151978 A1 | 12/2011 |
| WO | 2012086683 A1 | 6/2012 |
| WO | 2012111380 A1 | 8/2012 |
| WO | 2013008510 A1 | 1/2013 |
| WO | 2013061724 A1 | 5/2013 |

OTHER PUBLICATIONS

Anasari, K. I., et al., Fe(III)-salen and salphen complexes induce caspase activation and apoptosis in human cells, Journal of Biomolecular Screening, Jan. 16, 2011, vol. 16, No. 1, pp. 26-35.
Hille, A. et al, Effects of Metal Salophene and Saldach Complexes on Lymphoma and Leukemia Cells, Archiv der Pharmazie, Apr. 2011, vol. 344, No. 4, p. 217-223.
Larkworthy, L.F., et al., Mononitrosyl derviatives of iron and cobalt complexes of quadridentate ligands from 2-hydroxy-1-naphthaldehyde and ethylenediamine, Inorganica Chimca Acta, 1991, vol. 179, No. 2, p. 157-160.
Sharma, K. et al., Heterocyclic complexes of palladium (II): template synthesis, spectroscopic studies and biochemical aspects, Heterocyclic Communications, 2001, vol. 7, No. 4, pp. 393-398.
Guo-Dong Liu, Interaction of Metal Complexes of Bis-(salicylidene)-ethylenediamine with DNA, Analytical Sciences, 16, 2000, 1255-1259.
Zhong, C. et al, Synthesis and oxygenation property of Fe(II), Co (II) and Ni(II)-Bis-benzoin-semiethylendediamine) complexes, Xiantan Dazue Ziran Kexue Xuebao, 1997, vol. 19, No. 3, pp. 59-62.
Numata, Y. et al, Synthesis and property of nitrosyl cobalt and nitrosyl iron complexes with some quadridentate ligands, Inorganica Chimica Acta, 1980, vol. 43, No. 2, p. 193-7.
International Search Report from corresponding International Application No. PCT/JP2012/062301 mailed on Jul. 31, 2012.
Belanzoni, P. et al, A theoretical approach to a chemical system convertible into a storage cell: carbon-carbon bonds functioning as electron donor and electron acceptor units, Journal of Molecular Catalysis A: Chemical, 2003, vol. 204-205, p. 787-792.
Howells, P.N. et al., Reactions of (4, 9-dimethyl-5, 8-diazadodeca-4, 8-diene-2, 11-dione)copper (II), (Cu(baen)) with isocyanates, Inorganic Chemistry, 1976, vol. 15, No. 1, p. 124-129.
Anasari, K.I., et al., Fe(III)-salen and salphen complexes induce caspase activation and apoptosis in human cells, Journal of Biomolecular Screening, Jan. 16, 2011, vol. 16, No. 1, pp. 26-35.
Larkworthy, L.F., et al., Mononitrosyl derviatives of iron and cobalt complexes of quadridentate ligands from 2-hydroxy-1-naphthaldehyde and ethylenediamine, Inorganica Chimca Acta, 1991, vol. 179, No. 2, p. 157-60.
Sharma, K. et al., Heterocyclic complexes of palladium (II): template synthesis, spectroscopic studies and biochemical aspects, Heterocyclic Communications, 2001, vol. 7, No. 4, p. 393-398.
Zhong, C. et al, Synthesis and oxygenation property of Fe(II), Co (II) and Ni(II)-Bis-benzoin-semiethylendediamine) complexes, Xiantan Dazue Ziran Kexue Xuebao, 1997, vol. 19, No. 3, p. 59-62.
Kristy Cochran et al. "cis-Diamminodichloronickel and Its Interaction With Guanine and Guanine-Cytosine Base Pair" vol. 13, No. 2, Apr. 2002, pp. 133-140.
Yong, S. et al, Toward understanding macrocycle specificity of iron on the dioxygen-binding ability: a theoretical study, Physical Chemistry Chemical Physics, 2011, vol. 13, No. 30, p. 13800-8.
Hiizu Iwamura "Design of Organic Ferromagnets" Feb. 1989, pp. 76-88.
International Search Report dated May 12, 2015.
T. Matsushita,et al "A Facile Synthesis of Unsymmetrical tetradentate schiff-base ligands and their copper(II) and nickel(II) complexes", Polyhedron, vol. 5, No. 3, Jan. 1, 1986, pp. 735-738.
A. A. Osowole, et al, "Synthesis and Characterization of some nickel(II)[bata]-Ketoamines and their adducts with 2,2'-bipyridine and 1, 10-phenanthroline", Synthesis and Reactivity in Inorganic and Metal-Organic Chemistry, vol. 32, No. 4, May 28, 2002, pp. 783-799.
H. Y. Liu et al, "An initial approach to biologically related bridged assemblies: pyridinethiolate-linked iron Fe4S4—Fe complex systems", Journal of the American Chemical Society, vol. 113, No. 25, Dec. 1, 1997, pp. 9529-9539.
A. Kotocova et al., "Monatshefte fib" Chemie Chemical Monthly Springer-Verlag 1994 Printed in Austria Electrochemical Behavior of a Series of Fe(III) Complexes with Tetradentate Schiff Base Ligands, Monatshefte für Chemic, Jan. 1, 1994, pp. 491-492.
Luiza Arakaki et al, "Thermal Study of chelates of Co(II), Cu(II), Ni(II), Cr(III), Mo(III), and Fe(III) with bis (acetylacetone) ethylenediimine on activated silica gel surface", Journal of Thermal Analysis and Calorimetry, Kluwer Academic Publishers, Dordrecht, NL, vol. 97, No. 2, Apr. 27, 2009, pp. 377-382.
Xiu-Juan Qi, et al "anti-Spin-Delocalization Effect in Co—C Bond Dissociation Enthalpies", Organometallics, ACS, Washington, DC, US vo.. 27, No. 12, Jan. 1, 2008, pp. 2688-2698.

SELF-MAGNETIC METAL-SALEN COMPLEX COMPOUND

TECHNICAL FIELD

The present invention relates to a new metal-salen complex compound having self-magnetic properties.

BACKGROUND ART

Generally, when a drug is administered to a living body, it reaches an affected site and exerts its pharmacological effects at that affected site, thereby exerting its therapeutic effects. On the other hand, even if the drug reaches tissue other than the affected site (that is, normal tissue), it will not be therapeutic.

Therefore, how to guide the drug to the affected site is important. A technique to guide the drug to the affected site is called drug delivery, which has been actively studied and developed recently. This drug delivery has at least two advantages. One advantage is that a sufficiently high drug concentration can be obtained at the affected site tissue. Pharmacological effects will not be seen unless the drug concentration at the affected site is a constant value or more. The sufficient therapeutic effects cannot be expected if the drug concentration is low.

The second advantage is that the drug is guided to only the affected site tissue and, therefore, adverse reactions to the normal tissue can be inhibited.

Such drug delivery is most effective for a cancer treatment by antitumor agents. Most antitumor agents inhibit the cell growth of cancer cells which divide actively, so that the antitumor agents will also inhibit the cell growth of even the normal tissue in which cells divide actively, such as bone marrow, hair roots, or alimentary canal mucosa.

Therefore, cancer patients to whom the antitumor agents are administered suffer adverse reactions such as anemia, hair loss, and vomiting. Since such adverse reactions impose heavy burdens on the patients, the fact is that the dosage needs to be limited and the pharmacological effects of the antitumor agents cannot be obtained sufficiently.

Alkyl antineoplastic drugs among such antineoplastic drugs are a generic term for antitumor agents having the ability to combine an alkyl group (—CH2—CH2—) with, for example, a nucleic acid protein and have the effects of alkylating DNA and inhibiting DNA replication, causing cell death. These effects work regardless of cell cycles, also works on cells of the $G_0$ period, has a strong effect on cells which grow actively, and tends to damage, for example, bone marrow, alimentary canal mucosa, germ cells, or hair roots.

Moreover, antimetabolite antineoplastic drugs are compounds having structures similar to those of nucleic acids or metabolites in a protein synthesis process, impairs cells by, for example, inhibiting synthesis of the nucleic acids, and specifically acts on cells of a mitotic period.

Moreover, antitumor antibiotics are chemical substances produced by microorganisms, have actions such as DNA synthesis inhibition and DNA strand breaking, and exhibit antitumor activity.

Also, microtubule inhibitors have antitumor effects by directly acting on microtubules that serve important roles to maintain normal functions of cells, for example, by forming spindles during cell division, locating cell organelles, and transporting substances. The microtubule inhibitors act on cells, which divide actively, and nerve cells.

Moreover, platinum preparations inhibit DNA synthesis by forming DNA strands, interchain bonds, or DNA protein bonds. Cisplatin is a representative drug, but it causes severe nephropathia and requires a large amount of fluid replacement.

Furthermore, parahormone antineoplastic drugs are effective against hormone-dependent tumors. Female hormones or anti-androgen drugs are administered to an androgen-dependent prostatic cancer.

Furthermore, molecular targeted drugs are used for a treatment targeted at molecules that correspond to molecular biological characters specific to respective malignant tumors.

Moreover, topoisomerase inhibitors are enzymes for temporarily generating breaks in DNA and changing the number of tangles of DNA strands. A topoisomerase inhibitor I is an enzyme that generates breaks in one strand of a circular DNA, lets the other strand pass, and then closes the breaks; and a topoisomerase inhibitor II temporarily breaks both the two strands of the circular DNA, lets other two DNA strands pass between the former two strands, and reconnects the broken strands.

Furthermore, nonspecific immunopotentiators inhibit an increase of cancer cells by activating the immune system.

Now, as mentioned earlier, cancer patients to whom the antitumor agents are administered suffer adverse reactions such as anemia, hair loss, and vomiting. In consideration of such adverse reactions imposing heavy burdens on the patients, the dosage needs to be limited and the pharmacological effects of the antitumor agents may not be obtained sufficiently. In a worse-case scenario, there is fear that the patients might die due to the adverse reactions.

So, it is expected that cancer treatment can be provided effectively while inhibiting the adverse reactions by means of the drug delivery by guiding the anti-tumor agent to cancer cells and having the pharmacological effects exhibited and focused on the cancer cells. Topical anesthetics also have the same kind of problems. The topical anesthetics are used to treat topical itches and pains of, for example, mucosa or skin caused by hemorrhoidal disease, stomatitis, gum disease, cavities, tooth extraction, or operations. Lidocaine (product name: xylocaine) is known as a representative topical anesthetic; however, this lidocaine is faster-acting, but has an antiarrhythmic effect.

Furthermore, if lidocaine which is an anesthetic is injected into the spinal fluid when giving spinal anesthesia, lidocaine will spread through the spinal fluid; and in a worst-case scenario, there is fear that lidocaine might reach a cervical part of the spinal cord and thereby cause a respiratory function to stop and bring about critical adverse effects.

So, it is expected that cancer treatment can be provided effectively while inhibiting the adverse reactions by using the drug delivery to guide the anti-tumor agent to cancer cells and have the pharmacological effects exhibited and focused on the cancer cells.

It is also expected that the drug delivery can prevent diffusion of topical anesthetics, maintain the pharmacological effects, and reduce the adverse reactions.

An example of a specific method for the drug delivery is the use of a carrier. This is to load the carrier, which tends to concentrate on the affected site, with the drug and have the carrier carry the drug to the affected site.

A promising candidate of the carrier is a magnetic substance and there is a suggested method of attaching the carrier, which is the magnetic substance, to the drug and allowing the carrier to be accumulated at the affected site by a magnetic field (see, for example, Patent Literature 1).

However, when using the magnetic substance carrier as the carrier, it is difficult to aurally administer the magnetic substance carrier, molecules of the carrier are generally giant, and there are technical problems about binding strength and affinity between the carrier and the drug molecules; and because of the above-described reasons, it has been difficult to achieve the practical use of the magnetic substance carrier.

Therefore, a topical anesthetic is suggested in which side chains for giving positive or negative spin charge density are bonded to a basic skeleton of an organic compound, and which has suitability as a whole insofar as the topical anesthetic is guided by an external magnetic field; and if the topical anesthetic is applied to a human body or an animal, it is retained in an area where a magnetic field is applied topically by the magnetic field outside the body and the medicinal effects that the topical anesthetic originally has are exerted on the area. The above-mentioned technique uses an iron-salen complex as an example of such a drug (see Patent Literature 2).

Furthermore, a review article is introduced about an organic magnetic substance which creates magnets from high polymer materials by means of synthesis of "high-spin molecules" with more parallel spins than conventional metal magnetic substances (for example, see Non Patent Literature 1).

Furthermore, a technique that substitutes platinum contained in cisplatin with another element is also introduced (for example, see Non Patent Literature 2).

CITATION LIST

Patent Literature

[Patent Literature 1] Japanese Patent Application Laid-Open (Kokai) Publication No. 2001-10978

[Patent Literature 2] WO2008/001851

[Non Patent Literature 1] Hiizu Iwamura, "Molecular Design Aimed at Organic Ferromagnetic Substances," February 1989 issue, p.p. 76-88

[Non Patent Literature 2] Krsity Cochran et al., Structural Chemistry, 13 (2002), p.p. 133-140

SUMMARY OF INVENTION

Technical Problem

However, Non Patent Literature 1 and 2 do not state that the drug itself becomes magnetic.

It is an object of the present invention to provide a new self-magnetic metal-salen complex compound and its derivatives.

Solution to Problem

In order to achieve the above-described object, the present invention is characterized in that it is a new self-magnetic metal-salen complex compound represented by the following formula (I).

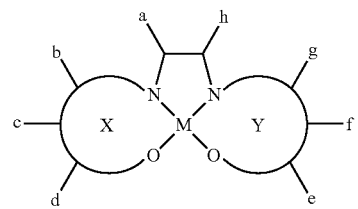

Each of X and Y is a five-membered ring structure including a coordinate bond between N and M, or its six-membered ring structure, wherein M is a bivalent metallic element composed of Fe (iron), Cr (chromium), Mn (manganese), Co (cobalt), Ni (nickel), Mo (molybdenum), Ru (rubidium), Rh (rhodium), Pd (palladium), W (tungsten), Re (rhenium), Os (osmium), Ir (iridium), Pt (platinum), Nd (niobium), Sm (samarium), Eu (europium) or Gd (gadolinium). If both X and Y are the five-membered ring structure, b and g do not exist and Formula (I) is any one of (i) to (iv).

(i) Each of a to h is hydrogen or any one of (A) to (G) mentioned below and —C(=O)m (where m is hydrogen or any one of (A) to (G) mentioned below);

(ii) each of (c, d) and (f, e) forms part of a heterocyclic structure and constitutes a condensate of the compound represented by Formula (I) and the heterocyclic structure, each of a, b, g, and h is hydrogen or any one of (A) to (G) mentioned below and —C(=O)m (where m is hydrogen or any one of (A) to (G) mentioned below), the heterocyclic structure is any one of three-membered to seven-membered ring structures containing furan, theophene, pyrrole, pyrrolidine, pyrazole, pyrazolone, imidazole, 2-isoimidazole, oxazole, isoxazole, thiazole, imidazole, imidazolidine, oxazoline, oxazolidine, 1,2-pyran, thiazine, pyridine, pyridazine, pyrimidine, pyrazine, orthoxadine, oxazine, piperidine, piperazine, triazine, dioxane, or morpholine, and a side chain for the heterocyclic structure is halogen, —R, —O—R (where R is one functional group selected from a hydrocarbon group including a methyl group), or hydrogen;

(iii) each of (c, d) and (f, e) forms part of one of condensed ring structures containing benzene or naphthalene and anthracene and forms a condensate of the compound represented by Formula (I) and the condensed ring structure, each of a, b, g, and h is hydrogen or any one of (A) to (G) mentioned below, and a side chain for the condensed ring structure is halogen, R—O—: (where R is one functional group selected from a hydrocarbon group including a methyl group), or hydrogen;

(iv) each of a and h forms part of a cyclic hydrocarbon structure containing a compound mentioned below and forms a condensate of the compound represented by Formula (I) and the cyclic hydrocarbon structure

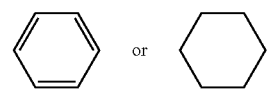 [SMILES: c1ccccc1 ; C1CCCCC1]

each of b to g and a side chain for the cyclic hydrocarbon structure is hydrogen or any one of (A) to (G) mentioned below.

(A) —CO$_2$R, —C(=O)R (where R represents hydrogen or chain or cyclic hydrocarbon having a saturated structure with carbon number 1 to 6 or an unsaturated structure (alkane or alkyne))

(B) —CO(OCH$_2$CH$_2$)$_2$OCH$_3$ (C)

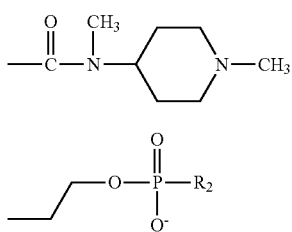

(D)

(where R$_2$ represents one of nucleic acids which are formed of adenine, guanine, thymine, cytosine, or uracil, or a plurality of the nucleic acids which are combined together);
(E) —NHCOH or —NR$_1$R$_2$ (where R$_1$ and R$_2$ represent hydrogen or chain or cyclic hydrocarbon with the same or different saturated structure with carbon number 1 to 6 or unsaturated structure (alkane or alkyne));
(F) —NHR$_3$—, —NHCOR$_3$, —CO$_2$—R$_3$, —S—S—R$_3$ or —R$_3$ (where R$_3$ represents hydrogen or a substituted compound as a result of elimination of a leaving group such as a hydroxyl group; and the substituted compound is functional molecules including at least one of enzymes, antibodies, antigens, peptides, amino acids, oligonucleotides, proteins, nucleic acids, and medical molecules); and
(G) halogen atoms such as chlorine, bromine, or fluorine.

The metal-salen complex compound represented by Formula (I) is a self-magnetic organic compound that does not contain a magnetic carrier. Therefore, another present invention is characterized in that it is a magnetic drug containing this metal-salen complex as an active ingredient and is administered into the body of a human or an animal and then guided to a target tissue by irradiating the human or animal body with an external magnetic field.

Furthermore, the metal-salen complex represented by Formula (I) is effective for treatment of tumors such as cancers. Therefore, another present invention is characterized in that it is an antitumor drug containing the magnetic drug as an active ingredient.

A system for guiding the metal-salen complex to the affected site is realized by supplying magnetic field to the metal-salen complex from outside the body by using the magnetic properties of the metal-salen complex. Therefore, another present invention is characterized in that it is a method for guiding a magnetic drug such as an anticancer agent containing the metal-salen complex as an active ingredient to the affected site by administering the magnetic drug into the body and then irradiating the body with an external magnetic field. Furthermore, another present invention is characterized in that it is a magnetic drug guiding system including a means for applying the magnetic drug into the body, a means for supplying a magnetic field to the drug applied to inside the body, and a means for moving the magnetic field to the affected site.

Advantageous Effects of Invention

According to the present invention, it is possible to provide a new metal-salen complex compound having self-magnetic properties, and magnetic drugs, antitumor drugs and a method and system for guiding magnetic drugs and antitumor drugs using such a new metal-salen complex compound.

DESCRIPTION OF EMBODIMENTS

Figure 1:
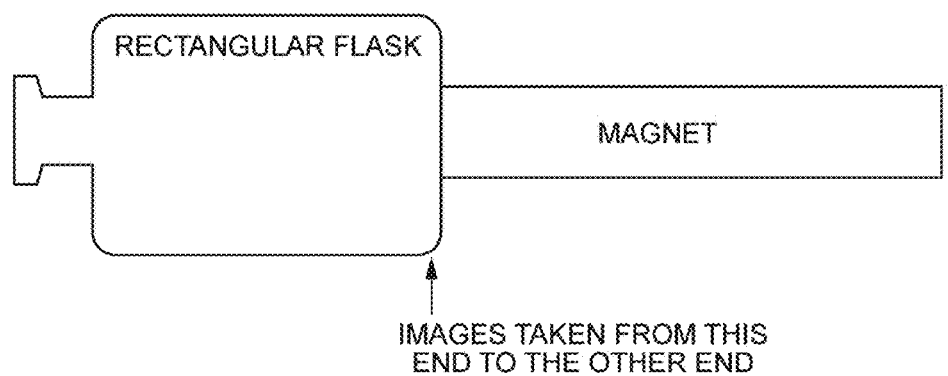
FIG. 1 is a diagrammatic illustration of a state where a bar magnet is made to be in contact with a rectangular flask containing a culture medium of rat L6 cells.

Preferred embodiments of the self-magnetic metal-salen complex compound represented by Formula (I) are (II) to (XI) below.

(II)
X, Y: six-membered ring structure
(a to h)=H

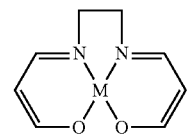

(III)
X, Y: six-membered ring structure
(c, f)=C(O)H
(a, b, d, e, g, h)=H

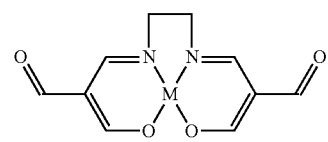

(IV)
X, Y: five-membered ring structure, (a, c, d, e, f, h)=H

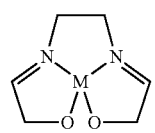

(V)
X, Y: six-membered ring structure
(a, b, g, h): H
(e, f), (g, h): constitute part of furan and furan is condensed with a main skeleton.
M: Fe

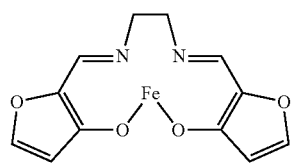

(VI)
X, Y: six-membered ring structure
(a, h): constitute part of cyclohexane and cyclohexane is condensed with a main skeleton.
(c, d), (e, f): constitute benzene
(b, g): H
M: Fe

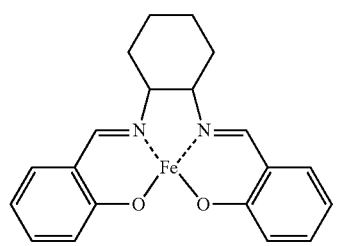

(VII)
X, Y: six-membered ring structure
(a, h): constitute part of benzene
(c, d), (e, f): constitute benzene
(b, g): H
M: Fe

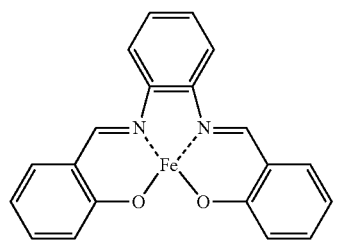

(VIII)
X, Y: six-membered ring structure
(c, d), (e, f): constitute anthracene
(a, b, g, h): H
M: Fe

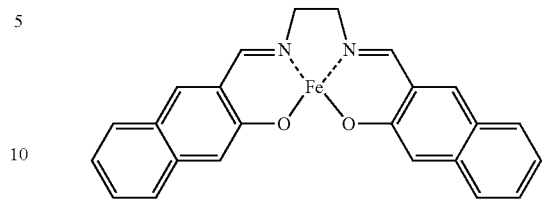

(IX)
X, Y: six-membered ring structure
(c, d), (e, f): constitute anthracene
(a, b, g, h)=H
Isomer of (V)
M: Fe

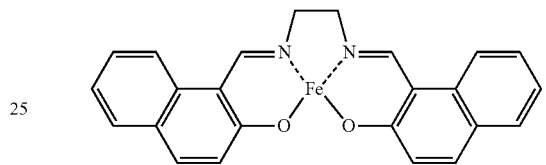

(X)
X, Y: six-membered ring structure
(c, d), (e, f): constitute benzene
Side chains at meta positions of benzene are halogens (bromine).
(a, b, g, h): H
M: Fe

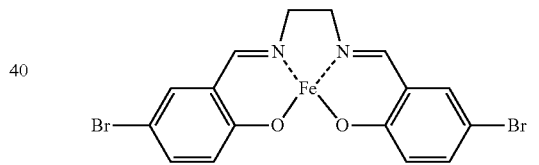

(XI)
X, Y: six-membered ring structure
(c, d), (e, f): constitute benzene
Side chains at meta positions of benzene are methoxyl groups.
(a, b, g, h): H
M: Fe

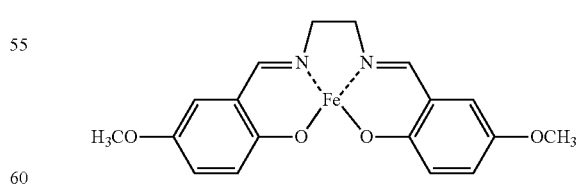

Since the metal-salen complex compound of Formula (I) has magnetic properties so that it can be guided by an external magnetic field, an absolute value of charge transfer of its side chain should preferably be less than 0.5 electrons (e). The substituted compound described in, for example, WO 2010/058280 can be used as the aforementioned $R_3$ which constitutes the above-described side chain. The content of the above-mentioned publication constitutes descriptions of the specification of this application.

As the metal-salen complex compound represented by Formula (I) is administered to inside the body and then guided to the target tissue by irradiating the body with the external magnetic field, the magnetic force strength of the metal-salen complex compound and the magnetization strength of the drug containing this metal-salen complex compound as an active ingredient are respectively within the range from 0.5 to 1.5 emu/g. The magnetic drugs are mainly injections or transfusions, or may be powdered drugs. Saline can be preferably used as a solvent for the injections or the transfusions. The magnetic drug contain the metal-salen complex as an active ingredient, for example, by 50 wt % or more; and in addition, the magnetic drug may contain diluents, stabilizing agents, and second active pharmaceutical ingredients which will have no or little influence on effectiveness, physical properties, or chemical properties of the metal-salen complex. The aforementioned metal-salen complex compound can be used as an anticancer agent.

Examples of the means for supplying a magnetic field to the magnetic drug after applying the magnetic drug into a human or animal body are permanent magnets or induction magnetic fields such as MRI. The strength of the external magnetic field should preferably be within the range of 0.5 to 1.0 T, or more preferably 0.8 to 1.0 T. Examples of the means for moving the magnetic field to the affected site include MRI besides an X-Y table for moving the permanent magnet. Examples of a form for supplying the magnetic field to the affected site tissues include a form for supplying the magnetic field from the body surface and a form for setting the magnetic field generating means at blood vessels near the affected site tissues. In order to supply the magnetic field from the body surface, there is a form for supplying the magnetic field from the front of the body and/or the back of the body.

EXAMPLES

Next, examples of the present invention will be explained.

Example 1

Synthesis of Metal-Salen Complex Compound (II)

First Synthesis Example

The metal-salen complex compound (II) was synthesized in accordance with the following reaction formulas.

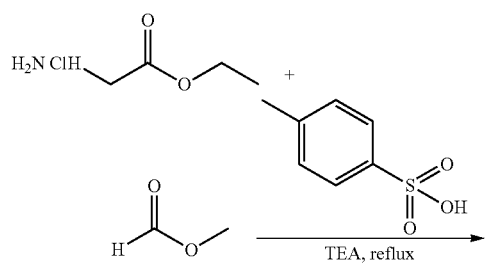

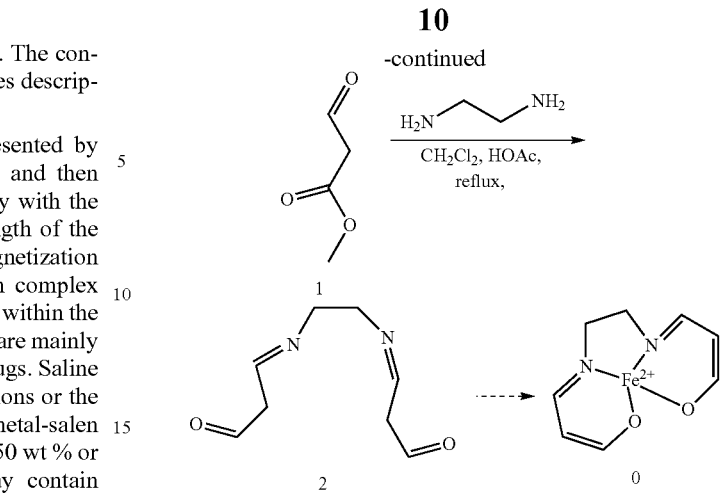

Synthesis of Compound 1

P-TsOH (10 mg) was added to an ethyl formate solution (60 ml) containing glycine methyl ester monohydrochloride (10.0 g, 0.079 mol) and the obtained solution was heated to boiling. Several drops of triethylamine were put into the solution while being boiled; and the mixed solution was brought to reflux for 24 hours and then cooled down to room temperature. Subsequently, white triethylaminehydrochloride was filtered and the residue was concentrated to 20 ml. The obtained solution was cooled down to a temperature of −5 degrees Celsius and then filtered. A reddish brown concentrated solution which was a residue (Compound 1) was obtained.

Synthesis of Compound 2

$CH_2Cl_2$ (20 ml) was dissolved in Compound 1. Then, ethane-1,2-diamine (1.2 g) and acetic acid (HOAc) (20 μl) were added to the obtained solution; and this reacted mixed solution was then brought to reflux for 6 hours. Subsequently, the reactant mixed solution was cooled down to room temperature, thereby obtaining 4 g of a yellow oil concentrate (Compound 2). Purity of the obtained Compound 2 was enhanced by flash column chromatography by using silica gel.

Synthesis of Compound 0

Compound 2 and triethylamine were introduced in methanol (50 ml) and a solution of metallic chloride ($FeCl_3(4H_2O)$ when synthesizing the iron-salen complex compound) was mixed in methanol (10 ml) in a nitrogen atmosphere. The mixture were mixed for one hour in a nitrogen atmosphere, thereby obtaining a brown compound. Then, this compound was dried in a vacuum, the obtained compound was diluted with dichloromethane (400 ml), washed twice with a saline solution, was dried over $Na_2SO_4$, and then dried in a vacuum, thereby obtaining Compound 0 (the metal-salen complex compound (II)).

Second Synthesis Example

The metal-salen complex compound (II) was synthesized in accordance with the following reaction formulas.

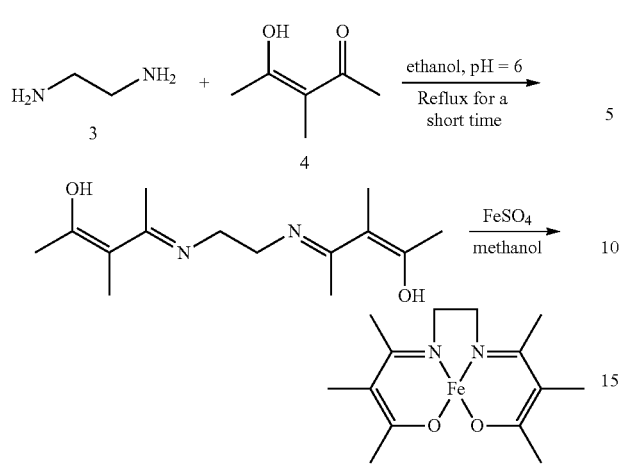

Compound 5 was synthesized by introducing 3.4 g of 3-methylacetylacetone (Compound 4) and 0.9 g of ethylene diamine (Compound 3) into anhydrous methanol (50 ml) while adjusting pH to pH 6 by using acetic acid on ice. The obtained solution was brought to reflux for 15 minutes and allowed to evaporate until its volume reduces to one half its original volume. Then, water of the same volume was added to the solution and let it deposit, thereby obtaining 1.4 g of white compound (Compound 5).

Subsequently, Compound 5 (1.2 g, 5 mmol) was introduced into methanol (50 ml) and FeSO$_4$.7H$_2$O (1.4 g, 5 mmol) was added to the obtained solution, thereby obtaining a pale bluish green solution. As this mixed solution was stirred for 8 hours at room temperature in a nitrogen atmosphere, its color gradually changed to brown. Subsequently, the solution was allowed to evaporate to reduce a half of its volume and then the same volume of water was added to the obtained solution. Next, vacuum was produced to allow methanol to evaporate, thereby obtaining brown lumps. These lumps were gathered, washed with water, and dried by producing a vacuum, thereby obtaining 360 mg of the target compound (the metal-salen complex compound (II)).

Third Synthesis Example

The metal-salen complex compound (II) was synthesized in accordance with the following reaction formulas.

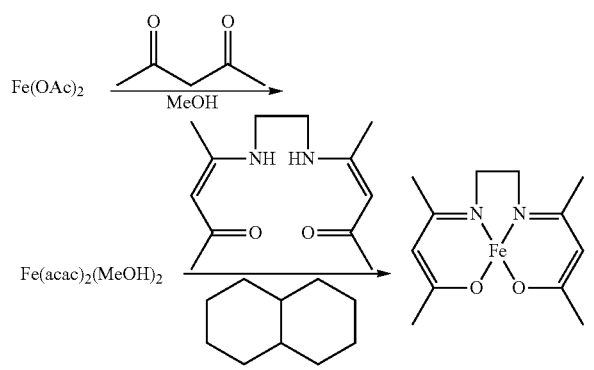

Iron (II) acetate (0.83 g, 4.8 mmol) and degassed methanol (48 ml) were introduced into a reaction container in a nitrogen atmosphere and acetylacetone (0.95 g, 9.5 mmol) was added to the obtained solution. The solution was stirred in a reflux for 15 minutes and then let it stand to cool. Deposited crystals were filtered and the obtained solution was washed with cooled methanol (10 ml). Subsequently, the solution was dried under reduced pressure, thereby obtaining 1.07 g of an intermediate.

The intermediate (1.07 g, 3.4 mmol), ligand atoms (0.70 g, 3.4 mmol), and degassed decalin (30 ml) were introduced into a reaction container in a nitrogen atmosphere and the obtained solution was stirred in a reflux for 1 hour. After letting the solution stand to cool and filtering a deposited solid, the obtained solid was washed with degassed cyclohexane (10 ml). Next, the solution was dried under reduced pressure, thereby obtaining 0.17 g of a product (the metal-salen complex compound (II)).

Example 2

Synthesis of Metal-Salen Complex Compound (III)

The metal-salen complex compound (III) was synthesized in accordance with the following reaction formulas.

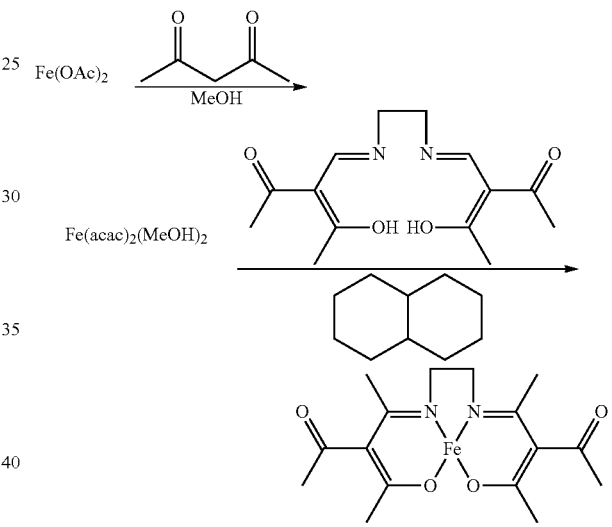

Iron (II) acetate (0.78 g, 4.5 mmol) and degassed methanol (20 ml) were introduced into a reaction container in a nitrogen atmosphere and acetylacetone (0.91 g, 9.9 mmol) was added to the obtained solution. The solution was stirred in a reflux for 15 minutes and then let it stand to cool. Deposited crystals were filtered, and the obtained solution was washed with cooled methanol (10 ml). Subsequently, the solution was dried under reduced pressure, thereby obtaining 0.58 g (yield 67%) of an intermediate.

The intermediate (240 mg, 0.75 mmol), ligand atoms (210 mg, 0.75 mmol), and degassed decalin (10 ml) were introduced into a reaction container in a nitrogen atmosphere and the obtained solution was stirred in a reflux for 30 minutes. After letting the solution stand to cool and filtering a deposited solid, the obtained solid was washed with degassed cyclohexane (3 ml). Next, the solution was dried under reduced pressure, thereby obtaining 101 mg of a product (the metal-salen complex compound (III)).

Example 3

Synthesis of Metal-Salen Complex Compound (IV)

The metal-salen complex compound (IV) was synthesized in accordance with the following reaction formulas.

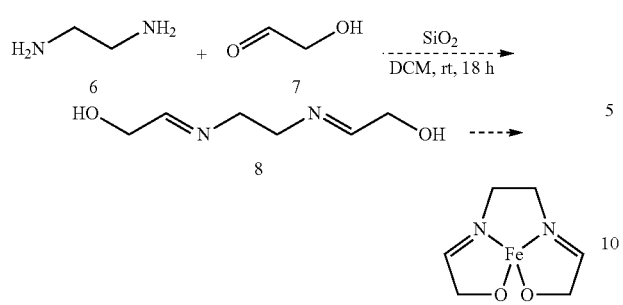

Iron (II) acetate (0.83 g, 4.8 mmol) and degassed methanol (48 ml) were introduced into a reaction container in a nitrogen atmosphere and acetylacetone (0.95 g, 9.5 mmol) was added to the obtained solution. The solution was stirred in a reflux for 15 minutes and then let it stand to cool. Next, Compound 7 (120 mg, 2.0 mmol) and $SiO_2$ (1 g) were added to a solution of Compound 6 (60 mg, 1.0 mmol) dissolved in $CH_2Cl_2$ (10 ml); and the obtained solution was stirred all night at room temperature to cause a reaction, thereby synthesizing Compound 8. Subsequently, the obtained Compound 8 together with iron (II) acetate (0.83 g, 4.8 mmol) and degassed methanol (48 ml) was introduced into a reaction container in a nitrogen atmosphere and acetylacetone (0.95 g, 9.5 mmol) was added to the obtained solution. The solution was stirred for 15 minutes in a reflux and deposited crystals were filtered, thereby obtaining a brown target compound (the metal-salen complex compound (IV)).

Example 4

The compounds (V) to (XI) were synthesized by a method described on pages 43 to 47 of a specification of WO2010/058280. Bromine or a methoxyl group which is a side chain is added to a main skeleton, when forming a metal complex bond to salen, by substituting a protecting group (NHBoc), which is bonded to a benzene ring at a para position with an OH group of the benzene ring, with bromine or the methoxyl group. With the compounds of (VIII) and (IX) in which (c, d) and (e, f) constitute anthracene, the following compound is used as a starting material instead of para-nitrophenol.

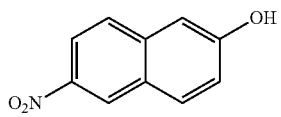 [SMILES: O=[N+]([O-])c1ccc2cc(O)ccc2c1]

Regarding synthesis of the metal-salen complex (VI) in which (a, h) constitute cyclohexane and the metal-salen complex (VII) in which (a, h) constitute benzene, the target salen before forming a coordinate bond with a metal is produced by a method described in Journal of Thermal Analysis and calorimetry, Vol. 75 (2004) 599-606, Experimental on page 600.

Example 5

Whether the aqueous solution of each metal-salen complex (II) to (XI) could be trapped by the permanent magnet or not was examined while having a pump circulate the aqueous solution in a glass tube. A circulation speed of the aqueous solution of the metal-salen complex was 100 mm/s, the diameter of the glass tube was 1.3 mm, the distance between the surface of the glass tube and the permanent magnet was 1.35 mm, and a concentration of the compound was 10 mg/ml. The magnet used was a commercially available bar magnet with a circular cross-section (20 mm in diameter; 150 mm long; model number N50 by Shin-Etsu Chemical Co., Ltd.; maximum magnetic flux density 0.8 T). Each metal complex was checked if it was trapped in an area where it traps on the magnet.

Example 6

Figure 2:
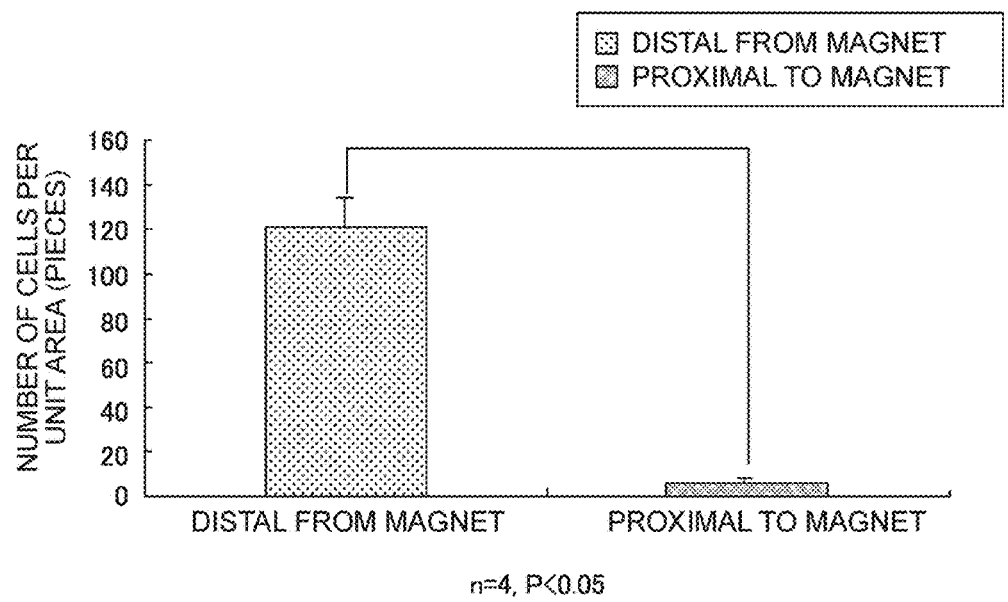
FIG. 2 is a graph showing the results of calculation of the number of cells as a result of taking photographs of a bottom face of the rectangular flask from its one end to the other end.

Regarding each of the metal (iron)-salen complexes (II) to (XI) obtained by the above-described methods, powder of the iron-salen complex compound (10 mg) was applied, to the degree allowing its magnetic attraction to be visibly observed, to a culture medium (PBS) when the rat L6 cells were in a 30% confluent state; and the state of the culture medium was photographed after 48 hours. FIG. 1 is a diagrammatic illustration of a state in which a bar magnet is in contact with a rectangular flask containing the rat L6 cell culture medium. After 48 hours, an image of the bottom of the rectangular flask was photographed from one end to the other end and the number of cells was calculated and the results are shown in FIG. 2. Referring to FIG. 2, a proximal position from the magnet indicates within a project area of the magnet end face on the bottom of the square-type flask and a distal position from the magnet indicates an area on the opposite side of the magnet end face on the bottom of the rectangular flask FIG. 2 shows that a concentration of each metal-salen complex increases as the metal-salen complex is attracted at the proximal position from the magnet; and it can be seen that the number of cells becomes extremely lower than that at the distal position due to a DNA-growth inhibition action of the complex. As a result, the drug can be concentrated at the target affected site or tissues of the individual by means of the metal-salen complex and the system including a magnetism-generating means.

Figure 3:
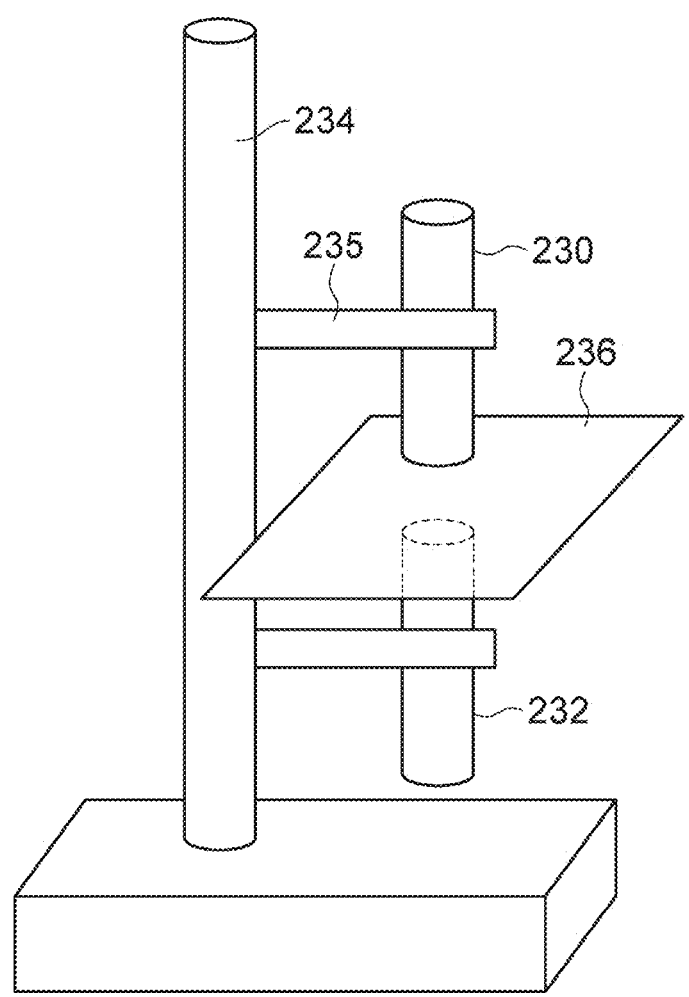
FIG. 3 is a perspective view of a magnetic guide device.

Next, a guide example using a guide device will be explained. With this guide device, as illustrated in FIG. 3, a pair of magnets 230 and 232 facing each other in the direction of gravity are supported by a stand 234 and a clamp 235, and a metal plate 236 is located between the magnets 230 and 232. A magnetic field of uniform strength can be created locally by placing the metal plate, especially an iron plate, between the pair of magnets. An electrical magnet can be used instead of the magnet to modify the magnetic force generated in this guide device. The magnetism-generating means can be moved to a target position of the individual on a table to allow the pair of magnetism-generating means to move in X, Y, and Z directions.

The drug can be concentrated on a specific tissue by placing a tissue in the region of the magnetic field. After intravenously injecting the aforementioned metal-salen complex (drug concentration: 5 mg/ml (15 mmol)) to a mouse weighing about 30 g, a laparotomy was performed, and the mouse was placed on the iron plate to locate its right kidney between the pair of magnets. The magnets used were Product No. N50 (neodymium permanent magnets) by Shin-Etsu Chemical Co., Ltd. with a residual flux density of 1.39 to 1.44 T. Under this circumstance, the magnetic field applied to the right kidney was about 0.3 T, and the magnetic field applied to its left kidney was about 1/10 of the above-mentioned magnetic field.

Figure 4:
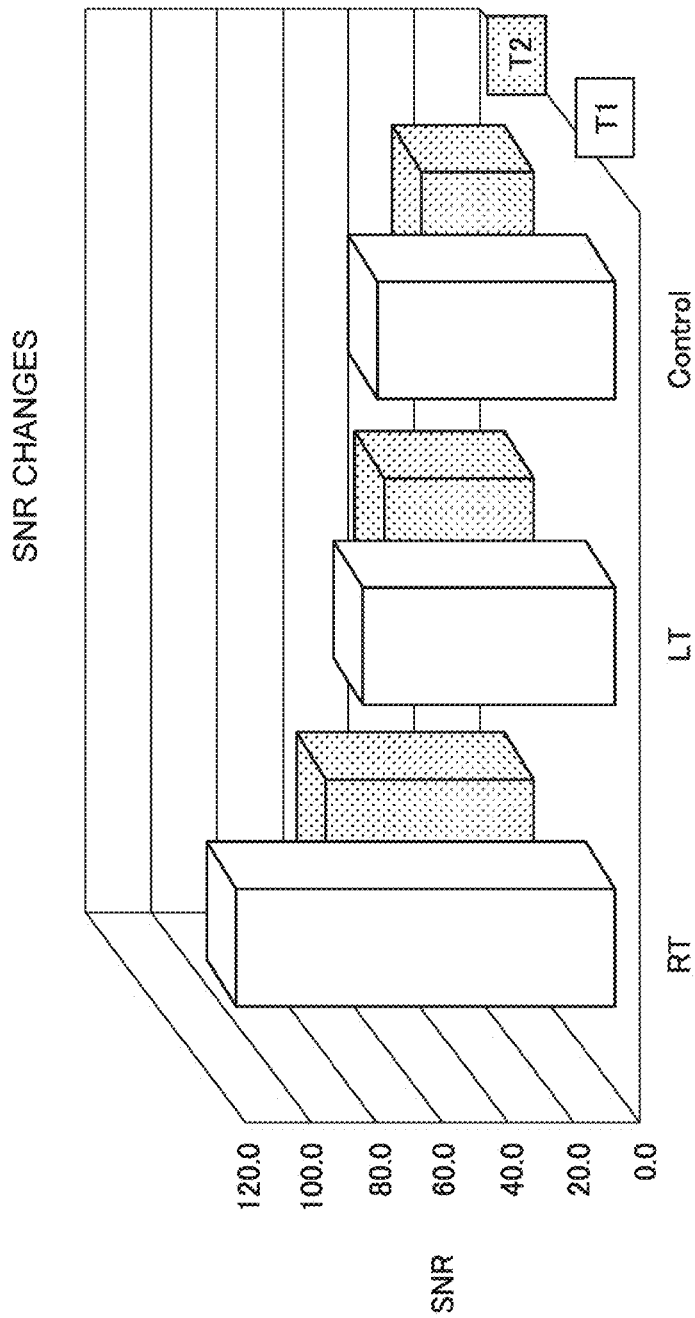
FIG. 4 is a graph showing MRI measurement results of kidneys to which a magnetic field was applied after intravenously injecting a metal-salen complex to mice.

Together with the left kidney and a kidney to which no field was applied (Control), a magnetic field was applied to the right kidney of the mouse; and after 10 minutes the SNR was measured by MRI in T1 mode and T2 mode. As a result as shown in FIG. 4, it was confirmed that the drug stayed in the right kidney (RT) to which the magnetic field was applied, as compared to the left kidney (LT) and Control.

Figure 5:
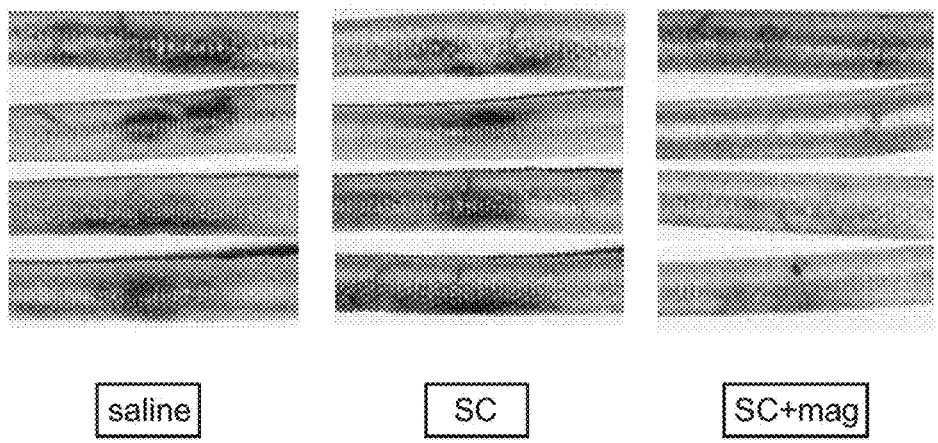
FIG. 5 is photographs of mouse tail tendon tissues showing the effects of the salen complex on melanoma growth in mice.

FIG. 5 shows the effect of the salen complex on melanoma growth in mice. Melanoma was established in mouse tail tendons in vivo by local grafting of cultured melanoma cells (Clone M3 melanoma cells). The salen complex (50 mg/kg) was administered intravenously via tail tendon vein, followed by local application of a magnetic field by using a commercially available bar magnet (630 mT, a cylindrical neodymium magnet, 150 mm long and 20 mm in diameter). Application of a bar magnet was performed with 3 hour gentle contact with the site of melanoma immediately after injection of the salen complex for 10-14 days.

Figure 6:
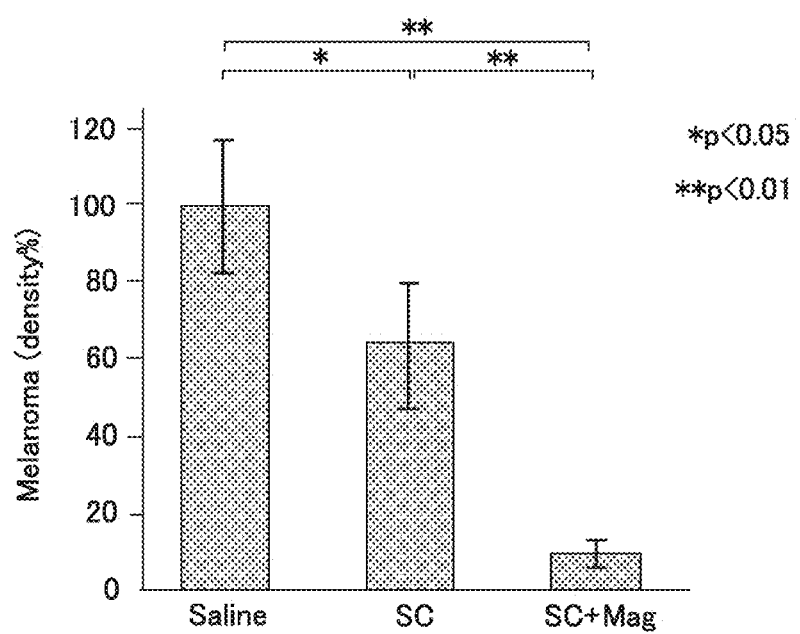
FIG. 6 is a graph showing the effects of the salen complex on melanoma growth in mice.

Application of the bar magnet was performed in such a way so that the magnetic field strength became maximal over the area of expected melanoma extension, which was approximately 150 mm or shorter in mouse tail tendons with the growth period of 2 weeks. Twelve days after the initial injection of the metal-salen complex, the extension of melanoma was evaluated by assessing the area of melanoma pigmentation. As shown in FIG. 6, the melanoma extension was greatest in the saline group (100±17.2%), in which saline was injected instead of the metal-salen complex.

Meanwhile, the melanoma extension modestly decreased (63.68±16.3%) in the SC group, in which the salen complex was injected without the application of a magnetic force field. In contrast, most melanoma disappeared (9.05±3.42%) in the SC+Mag group, in which the metal-salen complex was injected while applying a magnetic field.

Figure 7:
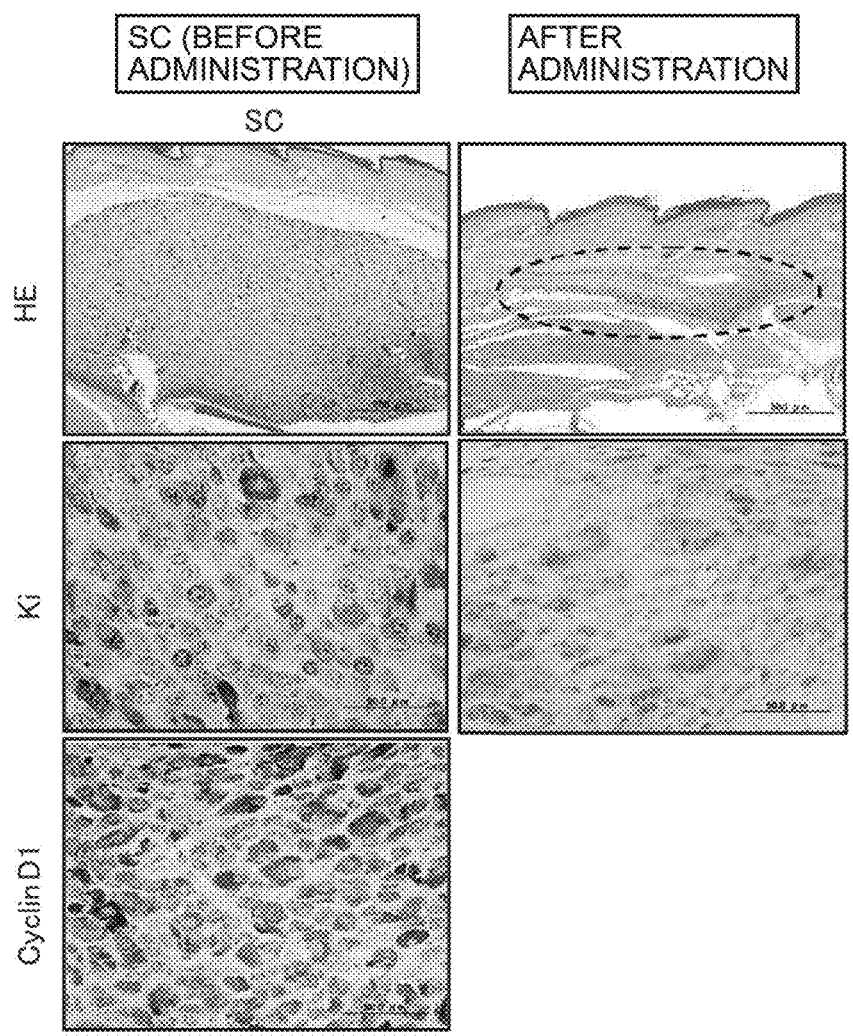
FIG. 7 is microphotographs showing the results of a histological examination indicating the effects of the salen complex on melanoma growth in mice.

A histological examination was performed as shown in FIG. 7 by means of Hematoxylin-Eosin staining (HE) and immunohistological staining (Ki, CyclinD1) with an anti-Ki-67 antibody and an anti-Cyclyn D1 antibody which are tumor proliferation markers in tissue sections. As a result, the histological examination revealed that tumor expansion of melanoma which was prominent before administration diminished when the metal-salen complex was injected (SC); and the tumor expansion of melanoma mostly disappeared after the application of the salen complex when the magnetic field application was combined with administration of the salen complex (as indicated as an ellipse in a dotted line in FIG. 7).

The invention claimed is:

1. An antitumor drug containing a magnetic drug containing a self-magnetic metal-salen complex compound represented by a formula (I), wherein the formula (I) is a following compound (II):

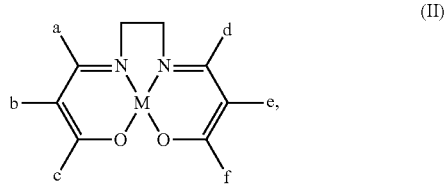

(II)

wherein M is Fe, and each of a-f is a methyl group, or each of the a-f is a hydrogen, or each of b and e is a hydrogen and a, c, d, and f is a methyl group, and wherein the magnetic drug being guided to a target tissue by administering the magnetic drug into a body and then irradiating the magnetic drug with an external magnetic field.

2. The antitumor drug of claim 1, wherein each of the a-f is hydrogen.

3. The antitumor drug of claim 1, wherein each of the a-f is a methyl group.

4. The antitumor drug of claim 1, wherein each of the a, c, d and f is a methyl group.

5. The antitumor drug of claim 1, wherein a charge transfer of a side chain of the metal-salen complex compound of the formula (I) is less than 0.5 electrons (e).

6. The antitumor drug containing the magnetic drug of claim 1, as an active ingredient.

7. A magnetic drug guiding system comprising:
a means for supplying a magnetic field to the drug stated in claim 1, and introduced into a body and a means for moving the magnetic field to an affected site.

8. A method of treating tumors using the antitumor drug according to claim 1, wherein the method comprises administering the antitumor drug into a body, guiding the antitumor drug to a target issue including tumors by applying an external magnetic field and diminishing tumor expansion.

9. The antitumor drug of claim 2, wherein a charge transfer of a side chain of the metal-salen complex compound of the formula (I) is less than 0.5 electrons (e).

10. The antitumor drug of claim 3, wherein a charge transfer of a side chain of the metal-salen complex compound of the formula (I) is less than 0.5 electrons (e).

11. The antitumor drug of claim 4, wherein a charge transfer of a side chain of the metal-salen complex compound of the formula (I) is less than 0.5 electrons (e).

12. The antitumor drug containing the magnetic drug of claim 2, as an active ingredient.

13. The antitumor drug containing the magnetic drug of claim 3, as an active ingredient.

14. The antitumor drug containing the magnetic drug of claim 4, as an active ingredient.

15. A magnetic drug guiding system comprising a means for supplying a magnetic field to the drug stated in claim 2, and introduced into a body and a means for moving the magnetic field to an affected site.

16. A magnetic drug guiding system comprising a means for supplying a magnetic field to the drug stated in claim 3, and introduced into a body and a means for moving the magnetic field to an affected site.

17. A magnetic drug guiding system comprising:
a means for supplying a magnetic field to the drug stated in claim 4, and introduced into a body and a means for moving the magnetic field to an affected site.

18. A method of treating tumors using the antitumor drug according to claim 2, wherein the method comprises administering the antitumor drug into a body, guiding the antitumor drug to a target issue including tumors by applying an external magnetic field and diminishing tumor expansion.

19. A method of treating tumors using the antitumor drug according to claim 3, wherein the method comprises administering the antitumor drug into a body, guiding the antitumor drug to a target issue including tumors by applying an external magnetic field and diminishing tumor expansion.

20. A method of treating tumors using the antitumor drug according to claim 4, wherein the method comprises administering the antitumor drug into a body, guiding the antitumor drug to a target issue including tumors by applying an external magnetic field and diminishing tumor expansion.

* * * * *